United States Patent [19]

Struble et al.

[11] 4,059,689

[45] Nov. 22, 1977

[54] ATTRACTANT FOR BEET WEBWORM MOTHS

[75] Inventors: Dean L. Struble; Charles E. Lilly, both of Lethbridge, Canada

[73] Assignee: Canadian Patents and Development Limited, Ottawa, Canada

[21] Appl. No.: 762,142

[22] Filed: Jan. 24, 1977

[30] Foreign Application Priority Data

Feb. 5, 1976 Canada .................................. 245075

[51] Int. Cl.$^2$ ............................................ A01N 17/14
[52] U.S. Cl. ...................................................... 424/84
[58] Field of Search .......................................... 424/84

[56] References Cited

PUBLICATIONS

Jacobson, "Insect Sex Pheromones" (1972) published by Acad. Press., N.Y. pp. 173, 248-250, 255, 262; 277-281 & 285.
Science, vol. 174, pp. 297-299, Oct. 15, 1971.
Nature, vol. 220, Nov. 9, 1968, pp. 600 & 601.
Chemical Abstracts, vol. 84: 55284K, Environ. Entomol. (1975), 4(5), pp. 822-824.

*Primary Examiner*—Donald B. Moyer
*Attorney, Agent, or Firm*—Alan A. Thomson

[57] ABSTRACT

A composite attractant (sex pheromone) for the male moths of the beet webworm (*Loxostege sticticalis*) comprises E-11-tetradecen-1-ol acetate; plus at least one of dodecan-1-ol acetate, dodecan-1-ol, tetradecan-1-ol, E-11-tetradecen-1-ol and E-11-tetradecenal, in minor proportions.

4 Claims, No Drawings

ATTRACTANT FOR BEET WEBWORM MOTHS

FIELD OF THE INVENTION

Composite attractants are described for male moths of the beet webworm (*Loxostege sticticalis* (Linnaeus)) which is a crop pest of inter alia sugar beets, rape, sunflowers, flax and clover and lucerne. The attractant is primarily intended for use in insect traps to monitor the population, but may also be useful for mass trappings or disruption of reproduction to aid in control of local outbreaks.

DESCRIPTION OF PRIOR ART

The life history of the beet webworm has been well documented but no reports have been noted concerning a sex pheromone or adult male moth sex attractant for this species. Currently light traps are being used to gauge the population density but these traps attract many species of moths that are flying at the same time making it very difficult to identify and count the desired species. Also the light traps are expensive and do not attract an accurate sample of the population. It would be beneficial to have a highly attractive and specific chemical attractant for this pest.

Recently, E-11-tetradecen-1-ol acetate has been found to be a component of the sex pheromone system of some other moths, e.g. the tufted apple bud moth (*Platynota idaeusalis*) and the European corn borer (*Ostrinia nubilalis*) moth. We have found that this compound is also an attractant for the beet webworm moth, but is non-specific for this species. It would be advantageous to provide a more attractive and more specific attractant than E-11-tetradecen-1-ol acetate for this species *Loxostege sticticalis*.

SUMMARY OF THE INVENTION

We have now found that a composite attractant comprising a mixture of a. E-11-tetradecen-1-ol acetate and b. at least one of dodecan-1-ol acetate, dodecan-1-ol, tetradecan-1ol, E-11-tetradecen-1-ol and E-11-tetradecenal, is a good species-specific attractant for male moths of the beet webworm. Component (b) is present in amounts enhancing the attractancy and specificity of (a), of less than about 30% of the mixture. The preferred concentration range for dodecan-1-ol and its acetate is about 2 to 10%; while the preferred range for tetradecan-1-ol, E-11-tetradecen-1ol and E-11-tetradecenal is about 10 to 25%.

DETAILED DESCRIPTION AND PREFERRED EMBODIMENTS

Laboratory bioassays were carried out in olfactometer cages with 81 synthetic compounds having from five to sixteen carbon atoms (mostly alcohols and acetates). The male moths of the beet webworm responded repeatedly only to 4 compounds listed in Table 1. These 4 compounds were tested at concentrations from 10 to 230 μg/carrier and only E-11-tetradecen-1-ol acetate (E11-14:Ac) at concentrations below 230 μg/carrier caused at least 50% of the males to attempt copulation. Results are summarized in Table 1.

Traps were made from 0.5 gallons (2 liters) cardboard containers with the bottom 2/3 of the inner surface coated with a sticky substance. The test chemical was placed on a rubber band which was hung in the center of the trap. Traps were set on wooden stakes 10 m apart in the field and were at a height of 1 m unless otherwise stated. The traps were placed in a single row in a north-south direction with one end of the trap facing the prevailing wind (west). The traps were placed along plots of rape and in fields of sugar beets. Treatments were replicated 4 times.

Initial field screening gave results corresponding to those of the olfactometer tests. E11-14:Ac at 10 or 20 μg/carrier gave greater catches than at 100 μg/carrier, and this compound tested more attractive than unmated females. Some screening results are given in Tables 2 and 3. These results indicate that E11-14:Ac should be present as a major component of a synthetic attractant and at some amount less than 100 μg/carrier. However, other field tests with E11-14:Ac clearly showed that this compound was not species-specific as in some cases greater numbers of other species were captured, particularly at trap heights below 1 m.

Further field tests were conducted to determine whether the attractancy of E11-14:Ac to beet webworm male moths could be enhanced by the addition of closely related compounds. Test data given in Table 4 shows that the addition to E11-14:Ac of E11-14:OH, tetradecan-1-ol (14:OH), dodecan-1-ol (12:OH) and dodecan-1-ol acetate (12:Ac) all increased the attractancy. Results varied somewhat for different flight periods. A total of 3,870 males were caught in the tests from August 8 to 28.

Some additional test results are given in Table 5 which tend to confirm a beneficial effect on adding 12:Ac, 12:OH or 14:OH to E11-14:Ac. However, the ambient population of moths were low during this test so that the results are not as significant as if the population and numbers of moths captured were larger.

The addition of 12:Ac, 12:OH, 14:OH or E11-14:OH to E11-14:Ac has been found to increase both the attractancy, and specificity for beet webworm moths, of the latter compound. Field traps should preferably be placed at a height of about 1 m for this species. The preferred dosage of total attractant per trap is from about 10 to 100 μg (in the absence of diluents etc.).

The compounds making up the attractant are available commercially or can be synthesized by known methods. E11-14:Ac used in the above tests was prepared by acetylating E11-14:OH, but E11-14:Ac is now commercially available. 12:Ac was obtained by acetylating 12:OH. The compounds need not be highly purified. The only isomer or normal impurity which was noted to act as inhibitor was Z11-14:Ac (mixtures of 5, 10 and 80% of the latter showed decreased attractancy compared to E11-14:Ac).

The attractant mixture was tested without further additives but inert fillers, diluents or carriers may optionally be present. Non-volatile inert liquids may serve as diluents or "keepers", reducing the volatility and prolonging the attractant effect. Such inert liquids may be for instance vegetable oils and mineral oils, e.g. rapeseed oil, corn oil, olive oil and pharmaceutical grade refined mineral oil. With these "keeper" liquids, the traps can be loaded with larger amounts of attractant giving longer trap life without serious suppression of attraction.

Recent test results have shown that, for the beet webworm, regular-shaped (non-conical) traps with a sticky inner surface and baited with a rubber dispenser, gave the best results, compared to polyethylene dispensers and conetype traps.

Table 1

Relative responses of adult beet webworm males to four compounds in the olfactometers

| Compound[a] | Concentration (μg)/carrier | Cages tested | Male responses[b] |
|---|---|---|---|
| E11-14:Ac(100) | 230 | 7 | +++ |
|  | 115 | 3 | +++ |
|  | 75 | 4 | +++ |
|  | 30 | 9 | +++ |
|  | 10 | 3 | ++ |
| Z11-14:Ac(98) | 230 | 2 | ± |
|  | 150 | 2 | + |
|  | 80 | 2 | + |
|  | 60 | 8 | ± |
|  | 30 | 7 | ± |
| E11-14:OH(99) | 230 | 2 | +++ |
|  | 200 | 2 | + |
|  | 60 | 6 | ± |
|  | 30 | 8 | + |
| E11-14:OH(98) | 230 | 2 | + |
|  | 150 | 2 | + |
|  | 60 | 6 | ± |
|  | 30 | 7 | ± |
| E11-14:Ac and E11-14:OH | 30:30 | 2 | +++ |
|  | 10:10 | 3 | ++ |
| E11-14:Ac and Z11-14:Ac | 60:60 | 2 | ++ |
|  | 60:30 | 2 | + |
|  | 10:10 | 2 | − |

[a]GLC purity (%) is given in brackets.
[b]Symbols: −, no response; ±, less than 50% of the males approached the air-intake and vibrated their wings; +, same as (±) but more than 50% responded; ++, 50% of the males had claspers extended while vibrating wings or while flying; +++, same as (++) with attempted copulations.

Table 2

Catches of beet webworm male moths along plots of rape with selected synthetic compounds from June 17 to July 23

| Synthetic Attractant Compound(s)[a] | Quantity (μg)/carrier | Total males captured/trap |
|---|---|---|
| E11-14:Ac | 10 | 39[b] |
| E11-14:Ac | 100 | 27[c] |
| E11-14:OH | 100 | 4 |
| Z11-14:Ac, 2% E11-14:Ac | 100 | 1 |
| E11-14:Ac, 20% Z11-14:Ac | 100 | 10 |
| E11-14:Ac, 80% Z11-14:Ac | 100 | 0 |
| E11-14:Ac, 50% E11-14:OH | 100 | 9 |
| Two unmated 2-day-old females | — | 6 |
| Unbaited trap | — | 0 |

[a]The GLC purity of the compounds was as follows: E11-14:Ac (100%); E11-1-4:OH(99%); Z11-14:Ac(98%), contained E11-14:Ac(2%).
[b]Average catch for 2 traps.
[c]Average catch for 4 traps.

Table 3

Catches of male beet webworm moths with selected compounds

| Compound(s)[a] | Quantity (μg)/of (μg)/carrier | no. captured[b] traps | Total males Beet webworm |
|---|---|---|---|
| E11-14:Ac | 20 | 2 | 85 |
| E11-14:Ac | 100 | 2 | 65 |
| Z11-14:Ac | 10 | 1 | 0 |
| Z11-14:Ac | 100 | 1 | 1 |
| E11-14:Ac, 5% Z11-14:Ac | 100 | 2 | 1 |
| E11-14:Ac, 10% Z11-14:Ac | 100 | 2 | 3 |
| E11-14:Ac, 30% E11-14:OH | 150 | 1 | 20 |
| E11-14:Ac, 60% E11-14:OH | 150 | 1 | 10 |

[a]The GLC purity of the compounds was as follows: E11-14:Ac(100%); E11-1-4:OH(99%); Z11-14:Ac(98%), contained E11-14:Ac(2%).
[b]The traps were placed in a field of sugar beets from July 4 to 30, and traps were sampled 12 times.

Table 4

Mean daily catches of male moths of the beet webworm with compounds at 50 μg per trap in field tests

| Treatment[a] | x males/trap for periods Aug. 8 to 19 | Aug. 19 to 28 | Aug. 8 to 28 |
|---|---|---|---|
| Unbaited trap | 0.0 | 0.0 | 0.0 |
| E11-14:Ac | 3.53 | 1.79 |  |
| E11-14:Ac, 2% E11-14:OH | 3.91 | — | — |
| E11-14:Ac, 6% E11-14:OH | 3.40 | — | — |
| E11-14:Ac, 10% E11-14:OH | 2.94 | — | — |
| E11-14:Ac, 15% E11-14:OH | 7.67[b] | 1.64 | 4.85 |
| E11-14:Ac, 20% E11-14:OH | 7.01 | 2.41 | 4.96 |
| E11-14:Ac, 6% 14:OH | 4.90 | — | — |
| E11-14:Ac, 15% 14:OH | 6.61 | 2.70 | 5.03 |
| E11-14:Ac, 6% 14:Ac | 2.35 | — | — |
| E11-14:Ac, 6% 12:OH | 11.1[b] | 2.05 | 6.80 |
| E11-14:Ac, 15% 12:Ac | 4.40 | 2.33 | 3.59 |
| E11-14:Ac, 6% 12:Ac | 8.23[b] | 3.48[b] | 6.96 |
| E11-14:Ac, 30% E11-14:OH |  | 2.62 | — |
| E11-14:Ac, 25% 14:OH |  | 3.00 | — |
| E11-14:Ac, 3% 12:OH |  | 1.89 | — |
| E11-14:Ac, 10% 12:OH |  | 2.18 | — |
| E11-14:Ac, 15% 12:Ac |  | 1.09 | — |

[a]All treatments were replicated 4 times and sampled 4 times during each period. A total of 3,870 male beet webwormmoths were captured from August 8 to 28.
[b]Significantly different (P < 0.05) from E11-14:Ac by the least significant difference test (Steel and Torrie, 1960).

Table 5

Mean daily catches of male moths of the beet webworm with compounds at 50 μg per trap in field tests from August 28 to September 26.

| Treatment[a] | x males/trap |
|---|---|
| Unbaited trap | 0.0 |
| One unmated female | 0.0 |
| E11-14:Ac | 0.26 |
| E11-14:Ac, 3% 12:Ac | 0.49 |
| E11-14:Ac, 6% 12:Ac | 0.43 |
| E11-14:Ac, 6% 12:OH | 0.40 |
| E11-14:Ac, 25% 14:OH | 0.39 |
| E11-14:Ac, 6% 12:Ac, 6% 12:OH | 0.23 |
| E11-14:Ac, 6% 12:Ac, 15% 14:OH | 0.23 |
| E11-14:Ac, 6% 12:Ac, 6% 12:OH, 15% 14:OH | 0.22 |
| E11-14:Ac, 15% E11-14:OH, 6% 12:Ac | 0.21 |
| E11-14:Ac, 15% E11-14:OH, 6% 12:Ac, 6% 12:OH | 0.20 |
| E11-14:Ac, 15% E11-14:OH, 6% 12:Ac, 15% 14:OH | 0.34 |
| E11-14:Ac, 15% E11-14:OH, 6% 12:Ac, 15% 14:OH, 6% 12:OH | 0.33 |

[a]All treatments were replicated 4 times and sampled 8 times. A total of 340 male beet webworm moths were captured (late in the season, ambient population low).

Several combinations of E-11-14:Ac with other compounds were field tested recently at 25 μg per rubber band dispenser in BAB-type stickem traps in four replications. The data obtained are summarized as follows:

Table 6(a)

Catches of beet webworm male moths

| Attractant Combination | Wt. Ratio | Total captured 15-28 June |
|---|---|---|
| E11-14:Ac | — | 176 |
| E11-14:Ac/E11-14:Ald | 5:1 | 183 |
| E11-14:Ac/E11-14:Ald | 1:5 | 138 |
| E11-14:Ac/Z11-14:Ald | 5:1 | 146 |
| E11-14:Ac/Z11-14:Ald | 1:5 | 86 |

Some additional combinations were tested (at 25 μg per rubber band dispenser in BAB-type stickem traps) in four replications from 16 July to 4 August in a field of sugarbeets. The data are summarized as follows:

Table 6(b)

Catches of beet webworm male moths

| Attractant Combination | Wt. Ratio | Total captured |
|---|---|---|
| E11-14:Ac | — | 122 |
| E11-14:Ac/E11-14:Ald | 10:1 | 123 |
| E11-14:Ac/E11-14:Ald | 1:1 | 151 |
| E11-14:Ac/E11-14:Ald /E11-14:OH | 20:4:1 | 115 |
| E11-14:Ac/E11-14:Ald /E11-14:OH | 20:4:4 | 135 |
| E11-14:Ac/E11-14:Ald /E11-14:OH | 20:4:10 | 142 |

The additive E-11-tetradecenal is seen to be beneficial in the attractant composition.

We claim:

1. A composite insect attractant for male moths of the beet webworm (*Loxostege sticticalis*) comprising a. E-11-tetradecen-1-ol acetate and b. a compound from the group dodecan-1-ol acetate, dodecan-1-ol, tetradecan-1-ol, E-11-tetradecen-1-ol and E-11-tetradecenal with (b) being present in small amounts enhancing the attractancy and species specificity of (a) to beet webworm moths, said amounts being from about 2 to about 10% by wt. of the mixture for the dodecyl compounds, and from about 10 to about 30% by wt. of the mixture for the tetradecyl compounds.

2. The composite attractant of claim 1 wherein (b) includes dodecan-1-ol or its acetate in amounts of from about 3 to about 10% by wt. of the mixture.

3. The composite attractant of claim 1 wherein (b) includes tetradecan-1-ol, E-11-tetradecen-1-ol or E-11-tetradecenal in amounts of from about 10 to about 25% by wt. of the mixture.

4. The composite attractant of claim 1 including an inert oil diluent.

* * * * *